United States Patent
Chen et al.

(10) Patent No.: US 7,900,806 B2
(45) Date of Patent: Mar. 8, 2011

(54) CIRCULAR STAPLER WITH AN AUTOMATIC SAFETY MECHANISM

(75) Inventors: Wang-dong Chen, Suzhou (CN); Jiang Lin, Suzhou (CN); Wei-zhong Yin, Suzhou (CN)

(73) Assignee: Suzhou Touchstone International Medical Science Co., Ltd., Suzhou (CN)

( * ) Notice: Subject to any disclaimer, the term of this patent is extended or adjusted under 35 U.S.C. 154(b) by 193 days.

(21) Appl. No.: 12/097,252

(22) PCT Filed: Nov. 15, 2006

(86) PCT No.: PCT/CN2006/003068
§ 371 (c)(1),
(2), (4) Date: Nov. 18, 2008

(87) PCT Pub. No.: WO2007/068181
PCT Pub. Date: Jun. 21, 2007

(65) Prior Publication Data
US 2010/0059571 A1 Mar. 11, 2010

(30) Foreign Application Priority Data
Dec. 14, 2005 (CN) ...................... 2005 2 0139728 U (51) Int. Cl.
*A61B 17/068* (2006.01)
(52) U.S. Cl. ................. 227/175.1; 227/175.2; 227/179.1
(58) Field of Classification Search ............... 227/175.2, 227/175.1, 179.1
See application file for complete search history.

(56) References Cited

U.S. PATENT DOCUMENTS

| | | | | |
|---|---|---|---|---|
| 4,383,634 A | * | 5/1983 | Green | 227/19 |
| 5,137,198 A | * | 8/1992 | Nobis et al. | 227/175.3 |
| 5,205,459 A | * | 4/1993 | Brinkerhoff et al. | 227/179.1 |
| 5,240,163 A | | 8/1993 | Stein et al. | |
| 5,271,544 A | * | 12/1993 | Fox et al. | 227/180.1 |
| 5,275,322 A | * | 1/1994 | Brinkerhoff et al. | 227/175.1 |

(Continued)

FOREIGN PATENT DOCUMENTS

CN 2364848 Y 2/2000

(Continued)

OTHER PUBLICATIONS

"International Search Report," Form PCT/ISA/210, issued for PCT/CN2006/003068, dated Mar. 8, 2007.

*Primary Examiner* — Rinaldi I. Rada
*Assistant Examiner* — Michelle Lopez
(74) *Attorney, Agent, or Firm* — Carstens & Cahoon, LLP (57) ABSTRACT

A circular stapler with an automatic safety mechanism comprises a stapler body, a stapler head, an actuating mechanism and a transmission adjusting mechanism; wherein the actuating mechanism comprises a handle and a handle coat, the transmission adjusting mechanism comprises a screw rod and an adjusting knob; a stopper is disposed either inside said handle or said handle coat; a safety rod and a pulling sheet are further provided, the safety rod has a safety block on one end and has a protruding block and a pin hole as its middle portion, a cylindrical pin is inserted into the pin hole so as to get the safety rod to be pivotally connected with the stapler body; the pulling sheet has a rear portion mounted on the screw rod and has a pulling hook at its front portion, the pulling hook hooks with the protruding block.

11 Claims, 6 Drawing Sheets

U.S. PATENT DOCUMENTS

| | | | | |
|---|---|---|---|---|
| 5,285,945 A | * | 2/1994 | Brinkerhoff et al. | 227/179.1 |
| 5,292,053 A | * | 3/1994 | Bilotti et al. | 227/179.1 |
| 5,333,773 A | * | 8/1994 | Main et al. | 227/179.1 |
| 5,350,104 A | * | 9/1994 | Main et al. | 227/179.1 |
| 5,533,661 A | * | 7/1996 | Main et al. | 227/176.1 |
| 5,782,396 A | * | 7/1998 | Mastri et al. | 227/175.3 |
| 5,988,479 A | | 11/1999 | Palmer | |
| 7,225,964 B2 | * | 6/2007 | Mastri et al. | 227/176.1 |
| 2005/0127131 A1 | * | 6/2005 | Mastri et al. | 227/176.1 |
| 2008/0017693 A1 | * | 1/2008 | Mastri et al. | 227/180.1 |
| 2008/0142566 A1 | * | 6/2008 | Gresham et al. | 227/179.1 |
| 2010/0096433 A1 | * | 4/2010 | Mastri et al. | 227/176.1 |

FOREIGN PATENT DOCUMENTS

CN      1252255 A      5/2000

\* cited by examiner

CIRCULAR STAPLER WITH AN AUTOMATIC SAFETY MECHANISM

FIELD OF THE INVENTION

The present invention relates to a surgical stapler used in surgery operations, more particularly, to a circular stapler with an automatic safety mechanism, which is in the technical field of medical instruments.

BACKGROUND OF THE INVENTION

A surgical stapler is a kind of medical instrument which is commonly used in surgery operations for intestinal or other tissue, the performance of the surgical stapler is very important to the success of whole surgery operation. A safety device is generally disposed on the surgical stapler in order to avoid mis-actuating. In prior art, most safety devices on circular staplers are operated manually, that is, when a doctor performs a surgery operation on a patient, the doctor does not release the safety device to perform actuations until he has already finished all the preparation works. But this kind of safety device has deficiencies identified in practice: if the doctor is less experienced, he may release the safety device to perform actuations in surgery operations even though the stapling distance is not in the right range, which leads to unwanted surgery operation results; or if the safety device is forgotten to be locked when replacing the stapler head assembly, it is very likely to grip the actuator trigger, accordingly the staples are shot out of the stapler head assembly, which leads to the failure of the surgery operation; some doctors may give a second actuation so as to avoid incomplete actuating, which results in tissue to be clamped into pieces. Therefore, the "safety device" and "device preventing second actuation" on this kind of stapler have become a research focus for people.

Regarding safety device, U.S. Pat. No. 5,193,731 disclosed a rotatable safety device disposed on an adjusting knob and U.S. Pat. No. 5,350,104 disclosed a safety device which is pivotally connected with a stapler body; both of the above mentioned staplers require the doctor to release the safety device manually when reaching the actuatable position. Chinese patent no. 99229088 disclosed an automatic safety device which is complex in assembling with too many parts and it is very difficult to get reset after being released; Chinese patent no. 99227301 disclosed a safety device by a safety rod propping against a screw rod, but the screw rod can be easily bent with this configuration.

Regarding the second actuation, Chinese patent no. 98121969 disclosed a safety device which can be automatically reset by a spring to prevent second actuation, which has deficiencies that: the spring is disposed outside the stapler body which increases the risk of clamping tissues, similarly the safety device props against the screw rod which can easily cause the screw rod bent. Due to the above mentioned reasons, according to the applicant's knowledge, —currently used staples in practice are not equipped with proper safety device to prevent the second actuation.

SUMMARY OF THE INVENTION

The invention is aimed at solving the problems of prior art surgical staplers by providing a circular stapler with an automatic safety mechanism, of which the safety mechanism can be operated automatically without manual operations thus improving safety and reliability to the surgery operations.

The object of the present invention is achieved by the following technical scheme:

A circular stapler with an automatic safety mechanism comprises a stapler body, a stapler head, an actuating mechanism and a transmission adjusting mechanism, wherein the actuating mechanism comprises a handle and a handle coat, the handle is connected with the handle coat and is pivotally connected with the stapler body, the transmission adjusting mechanism comprises a screw rod and an adjusting knob, the front end of the screw rod is connected with an anvil pulling rod while its rear end is connected with the adjusting knob by means of screw threads, wherein a stopper is disposed either inside said handle or said handle coat; a safety rod and a pulling sheet are further provided, the safety rod has a safety block on one end and has a second protruding block and a pin hole as its middle portion, a cylindrical pin is inserted into the pin hole so as to get the safety rod to be pivotally connected with the stapler body; the pulling sheet has a rear portion mounted on the screw rod and has a pulling hook at its front portion, the pulling hook hooks with second protruding block which is the middle portion of the safety rod; a restoring spring is provided so as to connect the safety rod with the stapler body, the safety rod is driven by the restoring spring to get reset by rotating anticlockwise around the cylindrical pin which connects the spring with the stapler body, until said safety block props against the stopper which is either disposed inside the handle or the handle coat.

Furthermore, said safety rod has a pointer on the other end, the pointer could be viewed from an indicator window which is disposed at a corresponding place of the stapler body; the restoring spring is disposed at a connection place of the safety rod and on a side where the pointer is located.

Furthermore, the front portion of said pulling sheet is divided longitudinally into at least three plates, and the pulling hook is the front portion of the middle plate; a first protruding block is disposed on the handle, when the handle is gripped, the first protruding block props against and pushes away said middle plate, thereby said pulling hook is disengaged from the second protruding block which is the middle portion of the safety rod.

Furthermore, the front portion of said pulling sheet is particularly divided into three plates, and the pulling hook is the front portion of the middle plate, the two side plates are respectively disposed in guide slots of the stapler body; and the middle portion of said screw rod has a small diameter portion.

Furthermore, the stopper is disposed inside the handle, said stopper and said handle are made into an integral; or, the stopper and the handle are separate parts with said stopper fixed on the two side walls of the handle.

Furthermore, the stopper is disposed inside the handle coat, said stopper and said handle coat are made into an integral; or, the stopper and the handle coat are separate parts with said stopper fixed on two side walls of said handle coat.

Furthermore, the stopper is a block part or a pin.

Furthermore, the handle and the handle coat are two separate parts, or they are made into an integral.

The stapler of the present invention has automatic safety protection function and prevents a second actuation, because the present invention provides a safety rod and a pulling sheet, wherein the pulling sheet works collaboratively with the first protruding block and a stopper which are disposed on the handle and the handle coat. Compared with the prior art, the stapler of the present invention is simple in structure, has good practicality, has fewer parts and is easily assembled. Before using, the safety block of the safety rod props against the stopper on or in the handle or handle coat so that the stapler can not be actuated, which provides an automatic safety protection; in the process of use, the safety rod rotates clockwise because of the pulling force from the pulling hook, when reaching the actuatable position, the safety block is automatically disengaged from the stopper, so that the doctor is able to perform the surgery operation immediately, it is more conveniently; then release the handle when finishing the actuation, the safety block of the safety rod is automatically return to against the stopper, this time, the pulling sheet is already disengaged from the second protruding block which is the middle portion of the safety rod, which prevents the stapler from a second actuation.

BRIEF DESCRIPTION OF THE DRAWINGS

Further features and advantages of the surgical stapler of the present, invention will become apparent from the following detailed description in combination with the appended drawings. Along with the embodiments mentioned above, the present invention is also available in other embodiments, that is, any technical schemes with same functions but in any of different forms are within the protection scope of the claims of the present invention.

in which: 1 denotes a handle; 2 denotes a handle coat; 3 denotes a safety rod; 4 denotes a screw rod; 5 denotes a pulling sheet; 6 denotes an adjusting knob; 7 denotes a first protruding block; 8 denotes a stopper; 9 denotes a rear portion of the pulling sheet; 10 denotes a pulling hook; 11a/b denote two side plates at the front of the pulling sheet; 12 denotes a pointer; 13 denotes a safety block; 14 denotes a second protruding block; 15 denotes a small diameter portion.

DETAILED DESCRIPTION OF THE PREFERRED EMBODIMENTS

As shown in FIGS. 1 to 14, a circular stapler with an automatic safety mechanism according to the present invention comprises a stapler body, a stapler head, an actuating mechanism and a transmission adjusting mechanism; wherein the actuating mechanism comprises a handle 1 and a handle coat 2, the handle 1 is connected with the handle coat 2 and is pivotally connected with the stapler body; the transmission adjusting mechanism comprises a screw rod 4 and an adjusting knob 6, a front end of the screw rod 4 is connected with an anvil pulling rod while its rear end is connected with the adjusting knob 6 by means of screw threads. Compared with the prior art, in the present invention, a restoring spring is disposed between the handle 1 and the stapler body, which keeps the handle 1 in an opening status all the time until the handle 1 is gripped.

Figure 7:
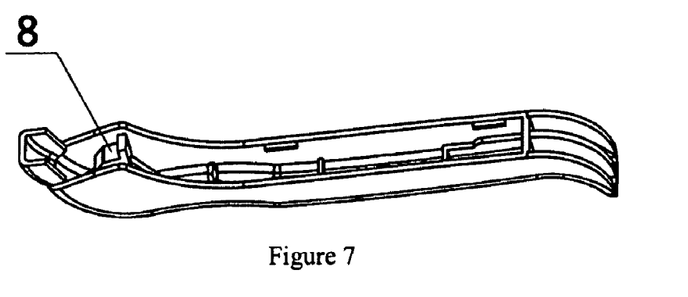
FIG. 7 is a perspective view of the handle coat of the stapler.
Figure 8:
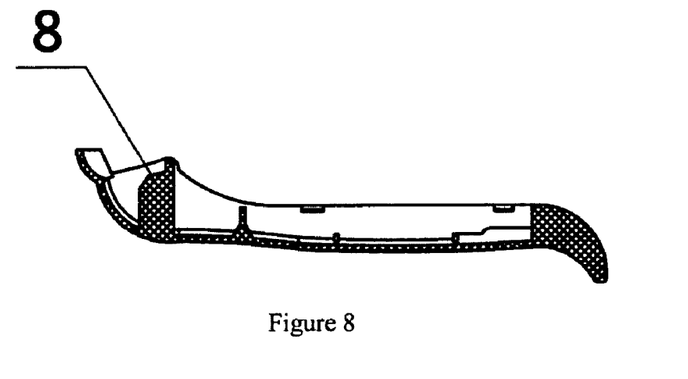
FIG. 8 is a longitudinal cross-sectional view of the handle coat of the stapler.

In another embodiment of the present invention, a stopper 8 is disposed inside the handle coat 2, as illustrated in FIGS. 7 and 8. A safety rod 3 and a pulling sheet 5 are further provided, the safety rod 3 has a safety block 13 on one end and a pointer 12 on the other end, the pointer 12 could be viewed from an indicator window which is disposed at a corresponding place of the stapler body. The safety rod 3 has a second protruding block 14 and a pin hole on its middle portion. A cylindrical pin is inserted into the pin hole so as to get the safety rod 3 to be pivotally connected with the stapler body. A restoring spring is provided so as to connect the safety rod 3 with the stapler body, the restoring spring is disposed at the connection place of the safety rod 3 and on the side where the pointer 12 is located, the safety rod 3 is driven by the spring to get reset by rotating anticlockwise around the cylindrical pin which connects the spring with the stapler body, so that the safety block 13 props against the stopper 8 which is disposed inside the handle coat 2 in the initial state and in the final state that finished firing and released the handle 1.

Figure 12:
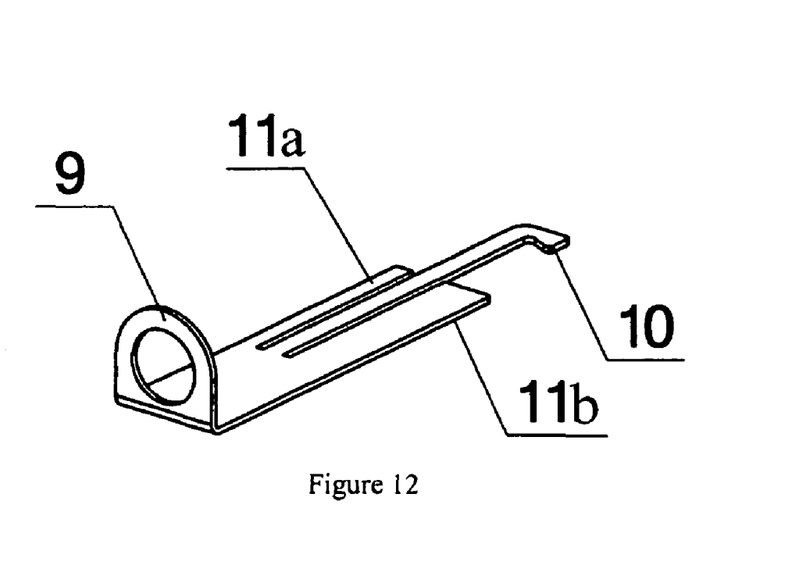
FIG. 12 is a perspective view of the pulling sheet of the stapler.
Figure 13:
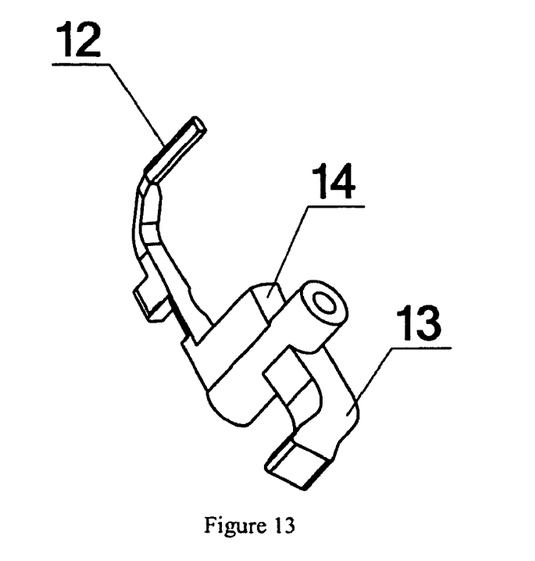
FIG. 13 is a perspective view of the safety rod of the stapler.

The pulling sheet 5 has a rear portion 9 mounted on the screw rod 4 and has a pulling hook 10 on its front portion, the pulling hook 10 hooks with the second protruding block 14 which is the middle portion of the safety rod 3. The front portion of said pulling sheet 5 is divided into three plates, and the pulling hook 10 is the front end of the middle plate, the other two side plates 11a and 11b are respectively disposed in guide slots of the stapler body. Furthermore, a first protruding block 7 is disposed on the handle 1, when the handle 1 is gripped, the first protruding block 7 props against and pushes away said middle plate, thereby the pulling hook 10 is disengaged from the second protruding block 14 which is middle portion of the safety rod 3.

Figure 1:
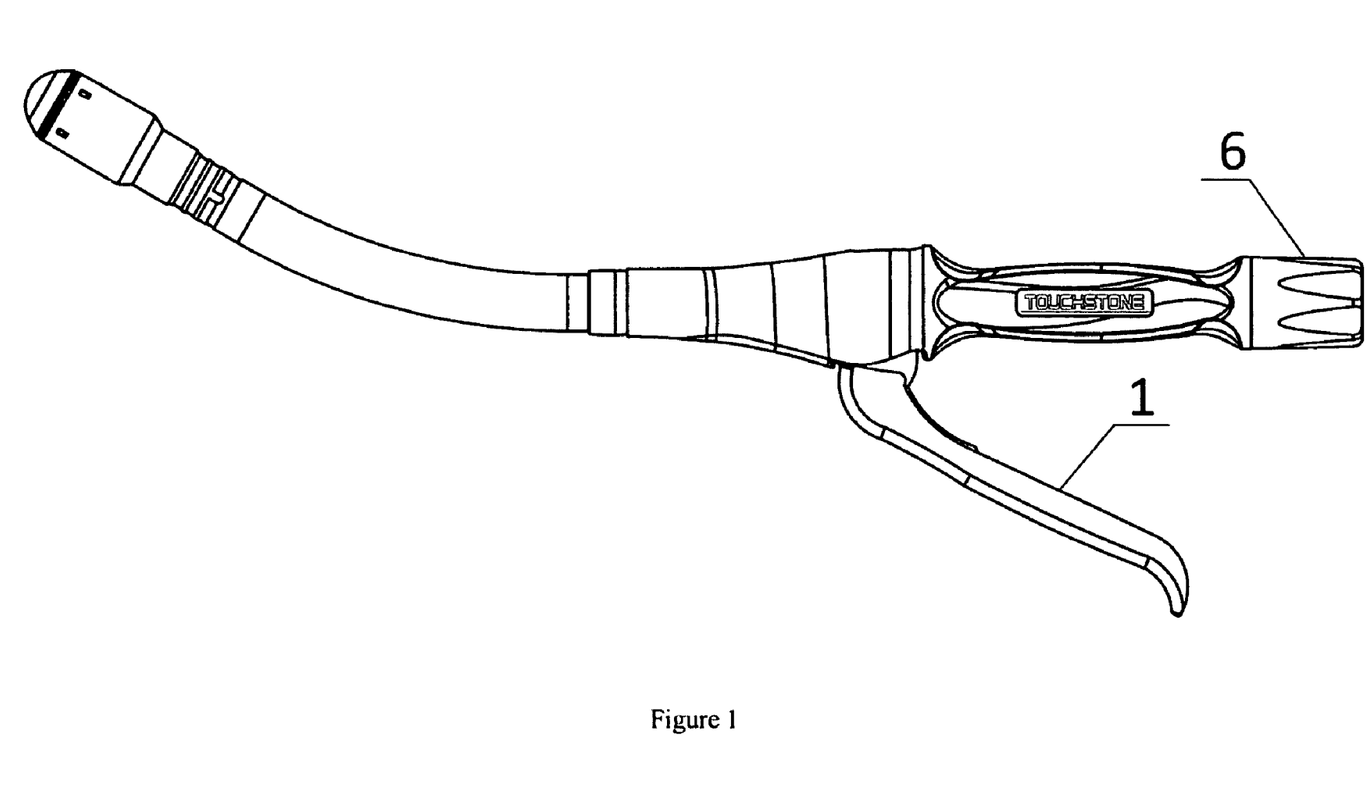
FIG. 1 is a schematic view showing the outline of a circular stapler with an automatic safety mechanism of the present invention.
Figure 2:
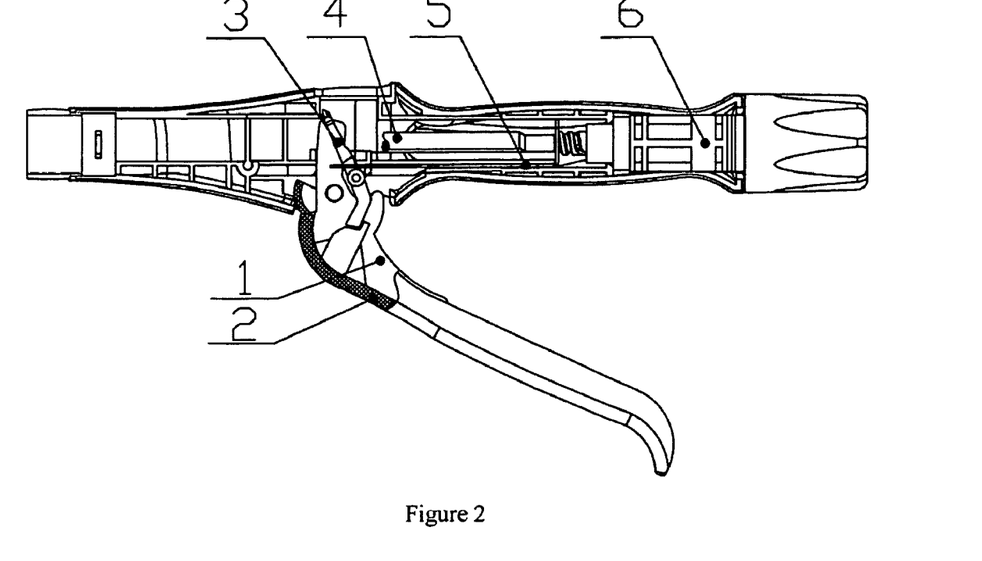
FIG. 2 is a cross-sectional view showing part of the stapler in initial state.
Figure 3:
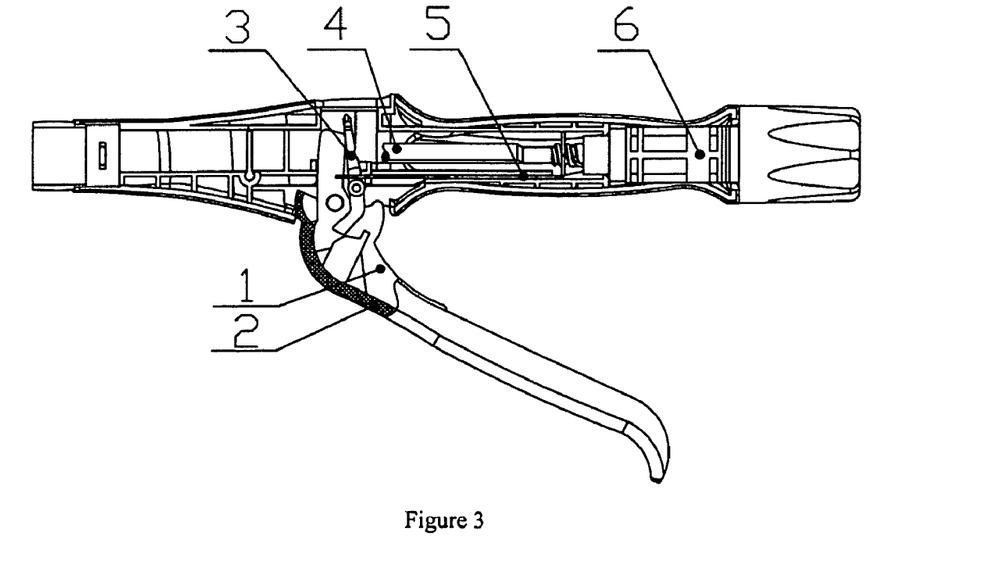
FIG. 3 is a cross-sectional view showing part of the stapler when reaching the actuatable position.
Figure 4:
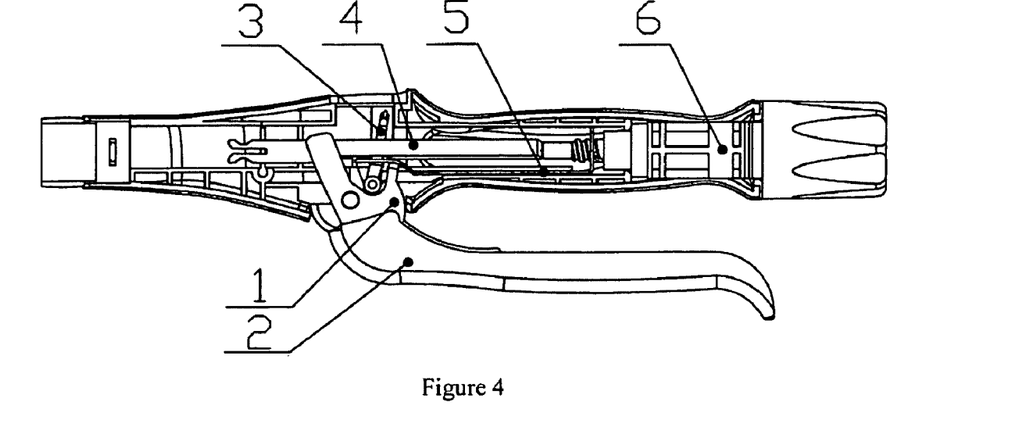
FIG. 4 is a cross-sectional view showing part of the stapler when the handle is gripped for actuation.
Figure 5:
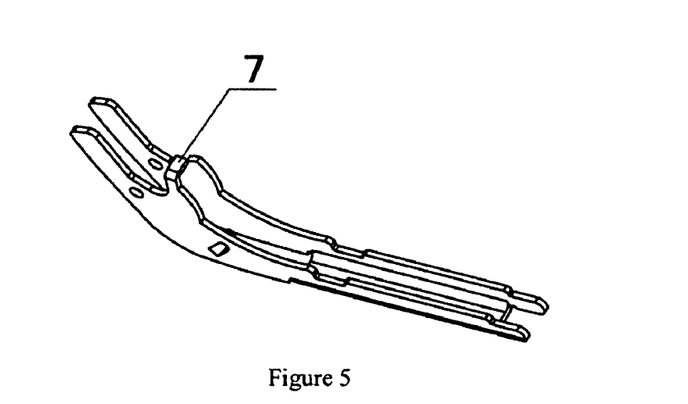
FIG. 5 is a perspective view of the handle of the stapler.
Figure 6:
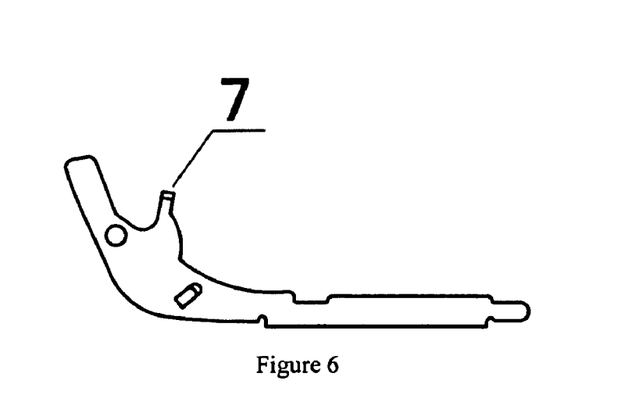
FIG. 6 is a two-dimensional structural view of the handle of the stapler.

When the stapler of the present invention is in the initial state, the safety block 13 which is one end of the safety rod 3 props against with the stopper 8 which is disposed inside the handle coat 2, so that the handle 1 and the handle coat 2 can not be gripped as illustrated in FIG. 2; in the process of use, rotate the adjusting knob 6 so that the screw rod 4 moves backward which drives the pulling sheet 5 to move backward, the pulling hook 10 at the front of the pulling sheet 5 hooks with the second protruding block 14 which is in the middle of the safety rod 3, so that the safety rod rotates clockwise around its axis, then the pointer 12 which is the other end of the safety, rod 3 is viewed from the indicator window of the stapler body, the safety block 13 which is one end of the safety rod 3 is gradually disengaged from the stopper which is disposed inside the handle coat 2 and gets completely disengaged when reaching the actuatable position, at this time the handle 1 can be gripped, that is, the automatic safety mechanism is closed as illustrated in FIG. 3; next, the surgery doctor holds the handle 1 to start stapling, the first protruding block 7 of the handle 1 props against the middle part of the pulling sheet 5 lead to the pulling sheet is distorted and move to a biased position, as a result, the pulling hook 10 at the front of the pulling sheet 5 is disengaged from the second protruding block 14 which is the middle portion of the safety rod 3 as illustrated in FIG. 4; release the handle 1, then the handle 1 gets reset to the initial state by the force from the restoring spring, also by the force from the restoring spring connecting with the safety rod 3 rotates anticlockwise to the initial place, that is, the place of automatic safety mechanism opened, at this time, the pulling sheet 5 can not pull the safety rod 3, so that the handle 1 can not be gripped, which prevents the second actuation.

Figure 14:
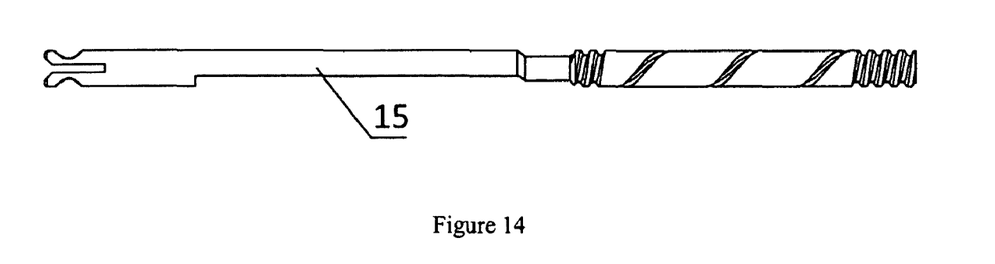
FIG. 14 is a two-dimensional structural view showing the screw rod of the stapler.

To ensure good implementation effect, the middle part of said screw rod 4 is preferably to be a small diameter portion 15, thereby enough movement space is made in the middle of the pulling sheet 5, and the pulling sheet 5 is driven to move by the force from the first protruding block 7 of the handle 1 so as to ensure the pulling hook 10 to disengage completely from the second protruding block 14 which is the middle portion of the safety rod 3.

Figure 9:
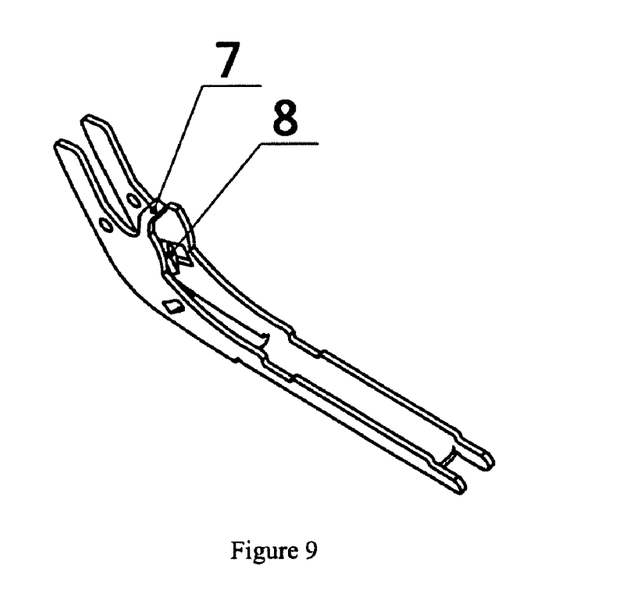
FIG. 9 is another perspective view of the handle of the stapler.
Figure 10:
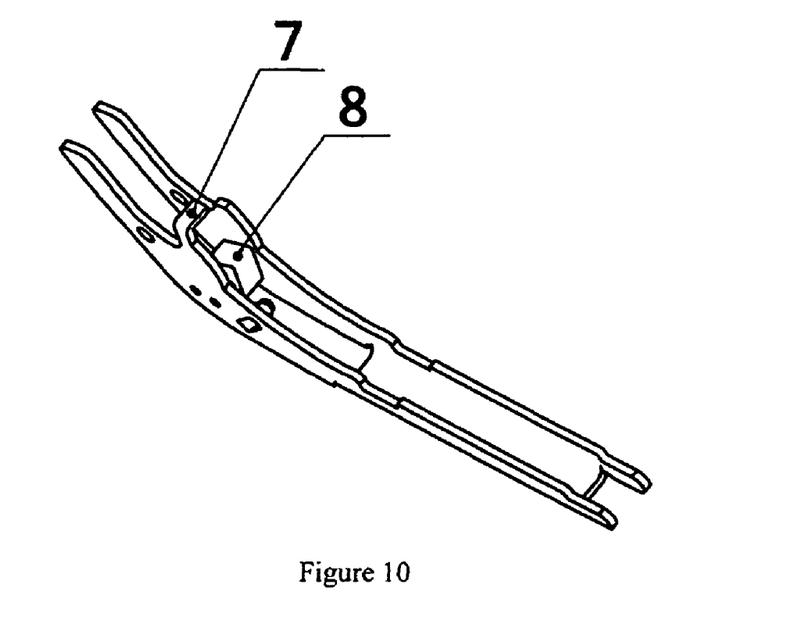
FIG. 10 is another perspective view of the handle of the stapler.
Figure 11A:
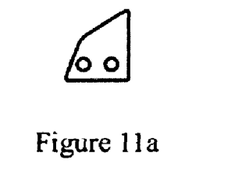
FIG. 11a is a front view of the stopper of the handle shown in FIG. 10.
Figure 11B:
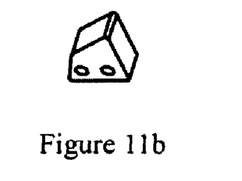
FIG. 11b is a perspective view of the stopper of the handle shown in FIG. 10.

The above mentioned embodiment is the stopper 8 disposed inside the handle coat 2 (as illustrated in FIGS. 7 and 8), besides, the stopper 8 can be disposed directly inside the handle 1. In this embodiment, the stopper 8 can be formed by punching the side walls of handle 1 inwardly, so that the stopper 8 and the handle 1 are made into an integral as illustrated in FIG. 9; or the stopper 8 and the handle 1 are two separate parts, the stopper 8 is fixed inside the handle 1 by means of two pins (alternatively, a non-cylinder shaped pin can be adopted for fixation) as illustrated in FIGS. 10, 11a and 11b. The stopper 8 can be a block part or to be made directly into a pin inserted on the two side walls of the handle.

Besides, it should be noted that, normally the handle 1 and the handle coat 2 are separate parts, the handle 1 is normally made from metal material and the handle coat 2 is made from synthetic materials of polymer, the handle 1 and the handle coat 2 are assembled together when they are made ready. Also, the handle 1 and the handle 2 can be made into an integral so as to have fewer parts.

What is claimed is:

1. A circular stapler with an automatic safety mechanism, comprising a stapler body, a stapler head, an actuating mechanism and a transmission adjusting mechanism; wherein the actuating mechanism comprises a handle (1) and a handle coat (2), the handle (1) is connected with the handle coat (2) and is pivotally connected with the stapler body, the transmission adjusting mechanism comprises a screw rod (4) and an adjusting knob (6), the front end of the screw rod (4) is connected with an anvil pulling rod while its rear end is connected with the adjusting knob (6) by means of screw threads, characterized in that: a stopper (8) is disposed either inside said handle (1) or said handle coat (2); a safety rod (3) and a pulling sheet (5) are further provided, the safety rod (3) has a safety block (13) on one end and has a second protruding block (14) and a pin hole as its middle portion; a cylindrical pin is inserted into the pin hole so as to get the safety rod (3) to be pivotally connected with the stapler body; the pulling sheet (5) has a rear portion (9) mounted on the screw rod (4) and has a pulling hook (10) at its front portion, the pulling hook (10) hooks with the second protruding block (14) which is the middle portion of the safety rod (3); a restoring spring is provided so as to connect the safety rod (3) with the stapler body, the safety rod (3) is driven by the restoring spring to get reset by rotating anticlockwise around the cylindrical pin which connects the spring with the stapler body, until said safety block (13) props against the stopper (8) which is either disposed inside the handle (1) or the handle coat (2); and wherein the front portion of said pulling sheet (5) is divided into at least three plates, and the pulling hook (10) is the front portion of the middle plate; a protruding block (7) is disposed on the handle (1), when the handle (1) is gripped, the protruding block (7) props against and pushes away said middle plate, thereby the pulling hook (10) is disengaged from said protruding block (14) which is the middle portion of the safety rod (3).

2. The stapler according to claim 1, characterized in that, said safety rod (3) has a pointer (12) on the other end, the pointer could be viewed from an indicator window which is disposed at a corresponding place of the stapler body.

3. The stapler according to claim 2, characterized in that, the restoring spring is disposed at a connection place of the safety rod (3) and on a side where the pointer (12) is located.

4. The stapler according to claim 1, characterized in that, the front portion of said pulling sheet (5) is divided into three plates, and the pulling hook (10) is the front portion of the middle plate, the two side plates (11a) and (11b) are respectively disposed in guide slots of the stapler body.

5. The stapler according to claim 1, characterized in that, the middle portion of said screw rod (4) has a small diameter portion (15).

6. The stapler according to claim 1, characterized in that, said stopper (8) is disposed inside said handle (1), said stopper (8) and said handle (1) are made into an integral; or, said stopper (8) and said handle (1) are separate parts with the stopper (8) fixed on the two side walls of the handle (1).

7. The stapler according to claim 6, wherein said stopper (8) is a block part or a pin.

8. The stapler according to claim 1, characterized in that, said stopper (8) is disposed inside said handle coat (2), said stopper (8) and said handle coat (2) are made into an integral; or, said stopper (8) and said handle coat (2) are separate parts with the stopper (8) fixed on two side walls of the handle coat (2).

9. The stapler according to claim 8, wherein said stopper (8) is a block part or a pin.

10. The, stapler according to claim 1, wherein said stopper (8) is a block part or a pin.

11. The stapler according to claim 1, characterized in that, said handle (1) and said handle coat (2) are two separate parts, or they are made into an integral.

\* \* \* \* \*